United States Patent [19]

Carmen et al.

[11] Patent Number: 5,102,407
[45] Date of Patent: Apr. 7, 1992

[54] BLOOD SEPARATION SYSTEM

[75] Inventors: Raleigh A. Carmen, Concord; Willie J. Lewis; Eva Sajan, both of Oakland, all of Calif.

[73] Assignee: Miles Inc., Elkhart, Ind.

[21] Appl. No.: 493,024

[22] Filed: Mar. 13, 1990

[51] Int. Cl.[5] .............................. C04B 5/02
[52] U.S. Cl. .................................. 604/410; 604/4; 604/408; 210/411
[58] Field of Search ........................ 604/4-6, 604/410, 406, 409, 408, 411; 210/206

[56] References Cited

U.S. PATENT DOCUMENTS

| | | | |
|---|---|---|---|
| 3,304,977 | 2/1967 | Hammons | 604/409 |
| 4,146,172 | 4/1972 | Cullis et al. | 604/410 X |
| 4,413,771 | 11/1983 | Rohde et al. | 604/410 X |
| 4,617,009 | 10/1986 | Ohlin et al. | 604/410 X |
| 4,810,378 | 3/1989 | Carmen et al. | 604/410 X |
| 4,895,275 | 1/1990 | Quinn et al. | 604/411 X |
| 4,917,804 | 4/1990 | Franks et al. | 604/410 X |
| 4,997,577 | 3/1991 | Stewart | 604/410 X |

*Primary Examiner*—Robert A. Hafer
*Assistant Examiner*—Kerry Owens
*Attorney, Agent, or Firm*—James A. Giblin; Elizabeth F. Enayati

[57] ABSTRACT

Blood bag system for separating whole blood into upper, middle, and lower components which can then be isolated from each other in an automated manner. The system comprises a primary or main blood bag having first and second outlet ports. The first outlet port communicates via tubing with a first satellite bag. The second outlet port communicates via tubing with a second satellite bag at one end and at the other end communicates with a tubular member extending into and toward the bottom of the main bag. In use whole blood is drawn into the main bag through an inlet port and centrifuged to form an upper, less dense plasma portion, a lower, more dense red blood cell (RBC) portion and an intermediate portion of buffy coat (including platelets). Pressure is then applied to the bag with the first outlet open and the second outlet closed to expres all of the upper plasma through the first outlet port after which the first outlet port is closed and the second outlet is opened. The lower RBCs are expressed by pressure through the tubular member and second outlet, leaving only the intermediate buffy coat in the main bag. The system may be automated with sensors to monitor and control the flow of fluids through each outlet and from the main bag.

11 Claims, 1 Drawing Sheet

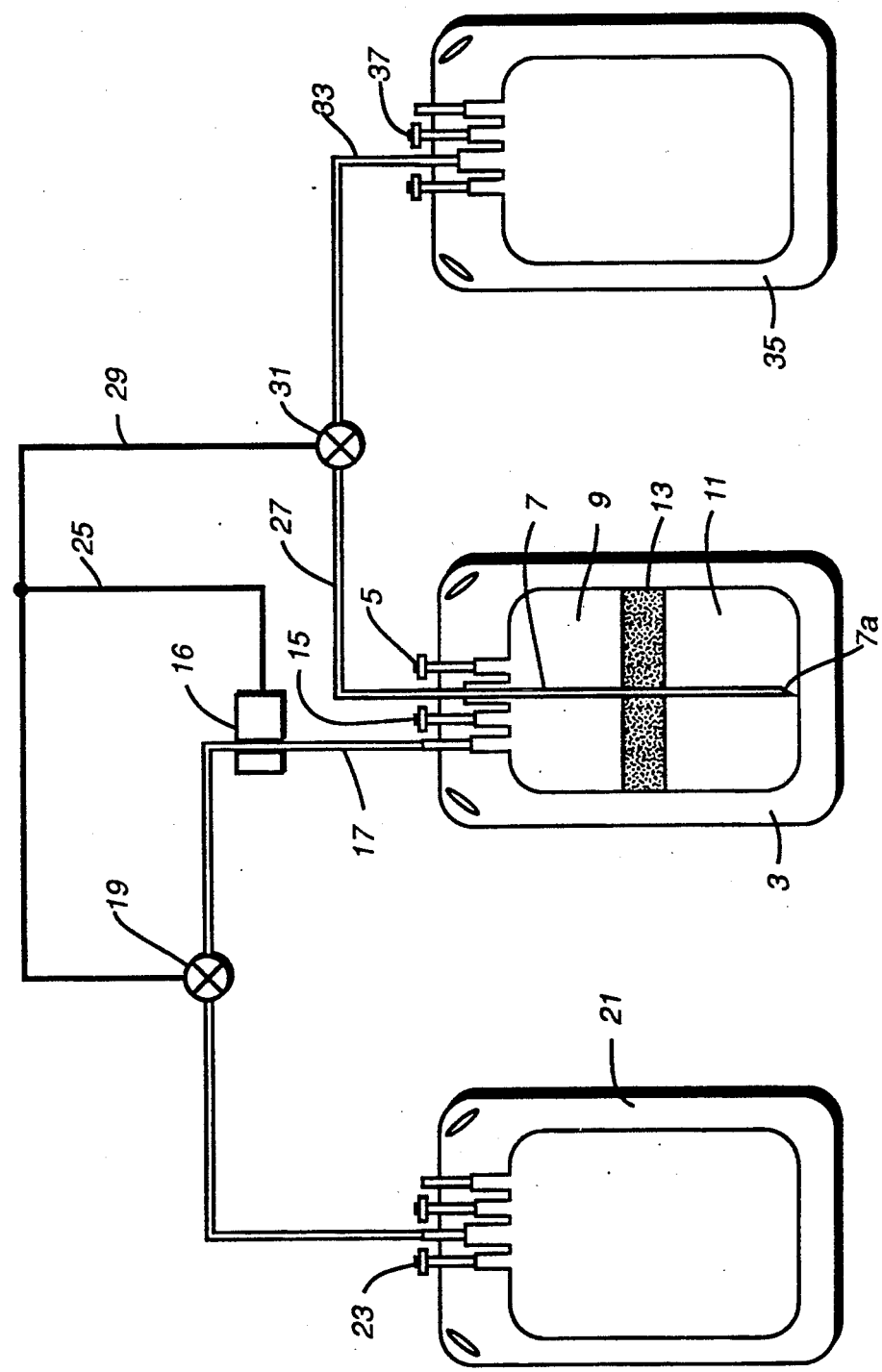

BLOOD SEPARATION SYSTEM

BACKGROUND OF THE INVENTION

1. Field

This disclosure is concerned generally with collection and separation systems for whole blood and specifically with a blood component separation system that can be partially automated.

2. Prior Art

Whole blood is commonly separated into its major components of less dense plasma and more dense red blood cells (RBCs) by first drawing the whole blood into a plastic bag known as a donor or primary bag. The bag's contents are then centrifuged under controlled conditions to result in a lower, more dense portion of packed RBCs and an upper less dense plasma portion, which may be rich in platelets (platelet rich plasma or PRP).

The donor bag is typically connected by plastic tubing to one or more satellite bags into which separated blood components (e.g. the PRP) may be expressed by external manipulation for further processing or use.

The above system for separating blood into its major components has remained virtually unchanged since the 1950's when plastic blood bags were introduced commercially on a large scale.

The classical method of preparing platelet transfusion products from whole blood collections consists of initial centrifugation of whole blood in a plastic blood bag at relatively low centrifugal force to separate most of the PRP from the red cells. The PRP is commonly expressed into an attached satellite blood bag. This is followed by centrifugation of the PRP in the satellite bag at relatively high centrifugal force to form a lower sediment of platelets and an upper platelet poor plasma (PRP). The sedimented platelets are in the form of a pellet or "button" which is resuspended in a small volume (50-60 mL) of donor plasma to give the platelet concentrate.

With good technique, about ⅔ of the platelets in a whole blood collection unit are recovered in the platelet concentrate. This is equivalent to about $8 \times 10^{10}$ platelets per concentrate. However, achieving this yield of platelets requires strict attention to centrifugation protocols, frequent calibration of the centrifuges, and operator diligence. The fact that the minimum standard for platelet yield is only $5.5 \times 10^{10}$ per concentrate attests to the operator-dependent nature of this procedure.

Recently, some transfusion services in Europe have begun to investigate and in some cases employ an alternate method of platelet preparation, specifically preparation from buffy coat. In this procedure the initial centrifugation of whole blood is performed at relatively high centrifugal force to form an upper layer of relatively cell-free plasma, an intermediate buffy coat layer containing platelets and leukocytes, and a lower layer of red cells.

The buffy coat plus either a small volume of plasma or a synthetic medium is then centrifuged at low centrifugal force to separate platelet concentrate (upper layer) from residual red cells and leukocytes. Data suggest that platelets prepared in this fashion are of improved quality, presumably because platelet activation that would otherwise occur during the pelleting step of the PRP centrifugation method is avoided.

The original work on buffy coat platelets was done at the Dutch Red Cross. Referred to as the Amsterdam method, it employed a standard quadruple plastic bag system. After centrifugation of blood and removal of plasma from the main bag, the buffy coat layer was transferred to an empty connected satellite bag and then processed to platelet concentrate. Using this method, Pietersz et al. (Vox Sang 1985; 49:81-85) found a mean of $7.2 \times 10^{10}$ platelets per concentrate; the volume of blood collected in this study was 500 mL. Kretschmer et al. (Infusionstherapie 1988; 15:232-239) found a mean of $6.3 \times 10^{10}$ platelets per concentrate from 450 mL blood collections.

The Amsterdam method, while apparently giving respectable platelet yields, was cumbersome and labor-intensive. The buffy coat transfer step required the operator to massage the bag to prevent hang-up of the "sticky" buffy coat layer. These manipulations might influence platelet function and release of granulocyte enzymes. There was also no way to control the volume of buffy coat removed.

Other efforts to improve platelet separation procedures or at least make it less burdensome are known. For example, U.S. Pat. No. 3,911,918 to Turner discloses a blood bag having an hour glass shape. That bag has a top portion for plasma, a bottom portion for RBCs and a middle portion for platelets and white blood cells. The hour glass shape is said to help position clamping or sealing devices at the juncture of the separated components after whole blood in the bag is centrifuged. This system has not been used on any significant commercial scale to date.

In U.S. Pat. No. 4,608,178 to A. S. Johansson and C. F. Hogman there is disclosed a "top/bottom" with which the upper and lower portions of separated blood components can be simultaneously expressed from a specially designed bag which leaves behind in the bag the intermediate portion known as buffy coat. The expression of that system is controlled by a pressure plate on the bag and sensors which monitor the position of the intermediate layer such that it remains in the bag while the upper plasma is expressed from a top part and the lower red blood cells are expressed from a bottom part in the bag. Hence, the name top/bottom bag. The sensors in that system assure the simultaneous expression of the top and bottom components.

The above described systems are fairly recent and it is not clear yet whether those systems will in time replace existing blood separation systems based on the use of a relatively simple unmodified donor bag.

However, the systems do offer new ways to prepare platelets (contained in the intermediate or buffy coat portion). The patent to Johansson and Hogman show how to do this in a semi-automated manner. Hence, it potentially represents a semi-automated way to prepare platelets.

In an effort to overcome problems associated with the Amsterdam method, Johansson and Hogman (see above-cited patent) developed the bag system with the top and bottom drainage of the primary bag and a sensor device which allowed partially automated blood separation. Kretschmer et al. used that type of system to prepare platelet concentrates from buffy coats and found a mean of $6.7 \times 10^{10}$ platelets per unit.

We have now found a novel alternative to the above described automated system, the details of which are described below.

SUMMARY OF INVENTION

Our system for separation of blood components comprises a main plastic bag having inlet and at least two outlet ports, all of the outlets being preferably at the top of the bag. One outlet port is in closed communication with or capable of being connected to an empty plasma satellite bag adapted to hold plasma. The other outlet port communicates at one end with a tube extending into the bag and close to the bag bottom and at the other end is in closed communication with or capable of being connected to a second bag adapted to hold red blood cells. In preferred embodiments the second satellite bag contains an RBC preservative solution such as AS-3.

In use, whole blood is drawn into the main bag via the inlet port and then centrifuged to form an upper, less dense plasma portion, an intermediate buffy coat portion (containing platelets) and a lower, more dense packed red blood cell portion. Pressure is then applied to the bag to express the upper plasma portion through the first outlet into the empty plasma satellite bag via a conventional blood bag connecting tubing. At a convenient location along the tubing is a sensor or photocell adapted to sense a color change as the last of the plasma (or first of the buffy coat) passes through the tubing. For example, the color change at the start or the top of the buffy coat portion can activate the sensor at which time the sensor activates a clamp (or valve) which closes the tubing connected to the first outlet port.

When the tubing of the first outlet is thus closed, the sensor simultaneously opens or activates a clamp (valve) in a tubing connecting the main bag with the second satellite bag adapted to hold red blood cells. This allows passage of the RBCs (from the tube extending into the bottom of the bag) to pass into the second satellite bag until a pre-determined volume of buffy coat remains in the main or primary bag. This leaves only buffy coat and platelets in the original bag.

BRIEF DESCRIPTION OF FIGURE

The FIGURE is a plan view of a preferred blood bag separation system of this disclosure.

SPECIFIC EMBODIMENTS

Our system for the separation of blood components and particularly for the preparation of platelet concentrate from buffy coat comprises a bag having sensor activated clamps or valves associated with each of the outlet ports as part of the bag. The outlet port for the RBCs communicates with a tubular extension extending to the bottom of the bag interior. In preferred embodiments, the tube is flexible to minimize breaking or bending during centrifuging. This also helps avoid bag puncture and breaking of the solvent bond where the tube connects to the outlet port. The tube is preferably transparent and extends to within about ⅛ inch of the interior bottom of the bag. Preferably, it is made from conventional blood bag PVC tubing and has a beveled tip to avoid blockage and assure fluid (RBC) flow even if the end of the tube actually touches or presses against the bag bottom.

A preferred system is a "triple" blood bag consisting of a primary or donor bag and two satellite bags preconnected to the primary bag by conventional blood bag tubing. The primary bag is made using conventional techniques but is modified in that the blood collection bag has a RBC outlet tube extending from a top outlet port to the bottom of the bag as shown in FIG. 1. All bags and connecting tubings are made from conventional blood bag plastics (e.g. PVC and the like) and are essentially transparent.

After collection of whole blood into bag 3, the triple unit is centrifuged at relatively high centrifugal force to form upper plasma component 9, intermediate buffy coat component 13, and lower red cell component 11. The bag 3 is then placed in a simple pressure-separator device (blood bag expresser) consisting of a moving spring-loaded expresser plate and a fixed plate. The separation system includes two on-off tubing clamps, 19 and 31, one on tubing 17 and one on tubing 27, activated by a sensor such as a photocell. Plasma passes through tube 17 while the tubing that conveys red cells passes through tube 27.

At the start of the plasma expression, a simple clamp 19 on tubing 17 is open and a simple clamp 31 on tubing 27 is closed. Plasma is expressed into bag 21 by pressure on bag 3 until red cells (in the buffy coat) are first detected in tubing 17 by the photocell sensor 19, at which time clamp 19 on tubing 17 closes in response to an electrical signal on wire line 25 from sensor 16 and the clamp 31 on tubing 27 opens in response to a signal on similar line 25. Red cells are then expressed from the beveled bottom 7a of tube extension 7 through the top of bag 3 into second satellite bag 35 containing a conventional red cell preservation solution such as AS-3 or the like (not shown). The expression continues until only a volume of about 50 mL (the buffy coat 13) remains in bag 3. This volume may be set, if desired, by a simple stop between the expresser plate and the backplate against which the bag 3 is pressed in an otherwise conventional blood bag expresser.

A preferred method of processing buffy coat to platelet concentrate after centrifugation is as follows. After the plasma and RBC expressions and detaching the plasma bag 21 and the red cell bag 35, the buffy coat 13 is held in the primary bag 3 overnight, preferably at room temperature with agitation. A number of bags containing buffy coat, preferably 6, are pooled together using a Sterile Connection Device (e.g. such as that shown in U.S. Pat. No. 4,507,119) into a bag containing a platelet additive solution. A platelet pooling bag such as that shown in U.S. Pat. No. 4,857,190 to S. Wada and B Kuhleman can be used. The pool of platelets is centrifuged at low centrifugal force to form an upper platelet concentrate (PC) layer and a lower layer of undesirable red cells and leukocytes. The PC may also be expressed through a leukocyte filter (e.g. as shown in U.S. Pat. No. 4,810,378 to R. A. Carmen et al) into a 1000 mL storage bag made of a plastic with high $O_2$ and $CO_2$ transmission rates for storage (e.g. as shown in U.S. Pat. No. 4,280,497 to Warner et al.).

EXAMPLE

The triple bag system of this invention was used to prepare components including buffy coat platelet concentrate from 6 individual units of blood. In this case the buffy coats were processed individually rather than as a pool. Whole blood was collected into a primary blood bag and the bag was centrifuged at $3000 \times g$ for 9 minutes. The plasma upper layer was expressed into an attached empty satellite bag followed by expression of red cell lower layer from the bottom and out of the top of the primary bag into an attached bag containing AS-3 RBC preservation solution.

About 50 mL of the intermediate buffy coat layer was left in the collection bag. Fifty milliliters of the plasma in the connected satellite bag was added back to the buffy coat. This was followed by overnight incubation of the primary bag contents at 22° C. on a flatbed shaker and centrifugation at 400×g for 6 minutes to separate platelet concentrate from residual red cells and leukocytes.

Platelet counts were performed on all fractions using either an electronic cell counter (plasma and platelet concentrate) or a manual method. Data are summarized in the table below.

TABLE

| Fraction | Platelets, No. × $10^{10}$ | Platelets % of Whole Blood |
| --- | --- | --- |
| Whole Blood | 12.8 ± 5.8 | — |
| Plasma | 1.4 ± 0.8 | 10.9 |
| Red Cells | 0.2 ± 0.1 | 1.6 |
| Platelet Concentrate | 8.7 ± 3.4 | 68.0 |
| Residual Buffy Coat | 2.1 ± 0.8 | 16.4 |

Data show that this system gives a very good yield of platelets into platelet concentrate (8.7±3.4×$10^{10}$ or 68%). Of note is the very low loss of platelets to the red cell fraction. Platelet losses to plasma and residual buffy coat fractions can be further reduced by optimizing centrifugation protocols.

Given the above disclosure it is thought variations will now occur to those skilled in the art. Accordingly, the above examples should be construed as illustrative and the scope of the invention disclosed herein should be limited only by the following claims:

We claim:

1. A system for separation for blood components and whole blood, the system comprising a blood bag having at least two outlet ports, a first outlet port and a second outlet port, the first port communicating with an output tubular member having an open end extending into the interior of the bag and terminating at a distance just above the bag bottom, establishing outflow path means for expressing a red blood cell layer near the bag bottom.

2. The system of claim 1 where the tubular member extends to within about ½ inches of the bottom of the bag's interior.

3. The system of claim 2 wherein the tubular member is flexible and terminates as a bevel.

4. The system of claim 1 wherein the second outlet port communicates with a first satellite blood bag via tubing.

5. The systems of claim 4 wherein the tubing communicating with an external clamp includes sensor means to stop passage of fluid through the tubing.

6. The system of claim 1 wherein the first outlet port communicates with a second satellite blood bag via tubing.

7. The system of claim 6 wherein the tubing communicating with an external clamp includes sensor means to stop passage of fluid through the tubing.

8. The system of claim 5 wherein the sensor means, upon sensing and stopping passage of fluid in the tubing, communicates with and opens an external valve on the tubing connecting the second outlet port with the blood bag so that fluid may pass from the bag through the outlet port to the second satellite bag.

9. A method of separating blood into components comprising the steps of
    (a) introducing whole blood into a blood bag having at least two outlet ports, a first one of the outlet ports communicating with a tubular member having an open end extending into the bag and ending within about a half inch of the bags interior bottom;
    (b) centrifuging the blood bag at relatively high centrifugal force to form an upper plasma portion, an intermediate buffy coat portion, and a lower red blood cell portion;
    (c) applying pressure to the bag to express the plasma portion through a second outlet port and out of the bag; and
    (d) applying pressure to the bag to express the red blood cell portion out of the bag through the open end of the tubular member and out of the bag.

10. The method of claim 9 wherein each outlet port is in closed communication via tubing with a satellite bag.

11. The method of claim 9 wherein the tubings connecting the satellite bags with the outlet ports include sensor means and valve means that cooperate in a predetermined manner to open and close fluid passage through the outlet ports.

* * * * *